US009357999B2

(12) United States Patent
Badhwar (10) Patent No.: US 9,357,999 B2
(45) Date of Patent: *Jun. 7, 2016

(54) AUTOMATIC SUTURING APPARATUS AND METHODS OF USE

(71) Applicant: Vinay Badhwar, Sewickley, PA (US)

(72) Inventor: Vinay Badhwar, Sewickley, PA (US)

(*) Notice: Subject to any disclaimer, the term of this patent is extended or adjusted under 35 U.S.C. 154(b) by 216 days.

This patent is subject to a terminal disclaimer.

(21) Appl. No.: 14/154,325

(22) Filed: Jan. 14, 2014

(65) Prior Publication Data

US 2014/0128966 A1    May 8, 2014

Related U.S. Application Data

(63) Continuation of application No. 13/096,815, filed on Apr. 28, 2011, now Pat. No. 8,663,249.

(60) Provisional application No. 61/329,340, filed on Apr. 29, 2010.

(51) Int. Cl.
| *A61B 17/04* | (2006.01) |
| *A61F 2/24* | (2006.01) |
| *A61B 17/062* | (2006.01) |
| *A61B 17/00* | (2006.01) |

(52) U.S. Cl.
CPC ........... *A61B 17/0469* (2013.01); *A61B 17/062* (2013.01); *A61F 2/2409* (2013.01); *A61B 17/0482* (2013.01); *A61B 17/0487* (2013.01); *A61B 17/0491* (2013.01); *A61B 2017/00783* (2013.01); *A61B 2017/047* (2013.01); *A61B 2017/0472* (2013.01); *A61B 2017/0488* (2013.01)

(58) Field of Classification Search
CPC ............. A61B 17/0469; A61B 17/062; A61B 2017/00783; A61B 17/0482; A61B 17/0491; A61B 2071/0472; A61B 2017/0488; A61B 17/0487; A61B 2017/047; A61F 2/2409
See application file for complete search history.

(56) References Cited

U.S. PATENT DOCUMENTS

| 4,898,155 A | 2/1990 | Ovil et al. |
| 5,417,700 A | 5/1995 | Egan |
| 5,735,862 A | 4/1998 | Jennings et al. |
| 5,769,863 A | 6/1998 | Garrison |
| 5,814,054 A | 9/1998 | Kortenbach et al. |
| 6,464,707 B1 | 10/2002 | Bjerken |
| 6,676,671 B2 | 1/2004 | Robertson et al. |
| 6,679,268 B2 | 1/2004 | Stevens et al. |

(Continued)

FOREIGN PATENT DOCUMENTS

| EP | 1229841 B1 | 8/2002 |
| EP | 1463451 B1 | 10/2004 |

(Continued)

OTHER PUBLICATIONS

International Search Report dated Jul. 22, 2011, issued in International Application No. PCT/US11/34353.

*Primary Examiner* — Julian W Woo
(74) *Attorney, Agent, or Firm* — Ramey & Schwaller, LLP (57) ABSTRACT

An automatic suturing apparatus comprises triggers that activate suturing and securing of the tissue of a patient. An automatic suturing apparatus also comprises triggers that activate suturing and securing of a valve to tissue of a patient. The automatic suturing apparatus can be used in systems and kits. An automatic suturing apparatus can be used in methods of suturing a tissue or a valve to tissue.

15 Claims, 9 Drawing Sheets

(56) References Cited

U.S. PATENT DOCUMENTS

| | | |
|---|---|---|
| 6,860,890 B2 | 3/2005 | Bachman et al. |
| 6,997,932 B2 | 2/2006 | Dreyfuss et al. |
| 7,270,671 B2 | 9/2007 | Fuseri et al. |
| 7,407,505 B2 | 8/2008 | Sauer et al. |
| 7,445,626 B2 | 11/2008 | Songer et al. |
| 7,670,370 B2 | 3/2010 | Hill et al. |
| 8,663,249 B2 * | 3/2014 | Badhwar ............... A61B 17/062 606/144 |
| 2004/0210305 A1 | 10/2004 | Shu et al. |
| 2005/0121042 A1 | 6/2005 | Belhe et al. |
| 2005/0222589 A1 | 10/2005 | Chu |
| 2006/0184203 A1 | 8/2006 | Martin et al. |
| 2006/0229675 A1 | 10/2006 | Novoa et al. |
| 2007/0255296 A1 | 11/2007 | Sauer |

FOREIGN PATENT DOCUMENTS

| | | |
|---|---|---|
| EP | 1628581 B1 | 3/2006 |
| EP | 1395180 B1 | 5/2008 |
| EP | 1511429 B1 | 7/2009 |
| WO | 9729694 A1 | 8/1997 |
| WO | 0239908 A2 | 5/2002 |
| WO | 2002094109 A1 | 11/2002 |
| WO | 2004103157 A2 | 12/2004 |
| WO | 2005070307 A2 | 8/2005 |
| WO | 2005112785 A2 | 12/2005 |
| WO | 2008048846 A2 | 4/2008 |
| WO | 2008051437 A1 | 5/2008 |
| WO | 2008051438 A2 | 5/2008 |
| WO | 2008051481 A2 | 5/2008 |
| WO | 2008058067 A1 | 5/2008 |
| WO | 2008097967 A2 | 8/2008 |
| WO | 2009035819 A1 | 3/2009 |
| WO | 2009108664 A2 | 9/2009 |
| WO | 2009137766 A1 | 11/2009 |
| WO | 2010025102 A1 | 3/2010 |
| WO | 201065912 A1 | 6/2010 |

* cited by examiner

AUTOMATIC SUTURING APPARATUS AND METHODS OF USE

CROSS-REFERENCE TO RELATED APPLICATIONS

The present application claims priority to U.S. patent application Ser. No. 13/096,815, filed Apr. 28, 2011, entitled AUTOMATC SUTURING APPARATUS AND METHODS OF USE, issued as U.S. Pat. No. 8,663,249, and to U.S. Provisional Patent Application No. 61/329,340, filed Apr. 29, 2010, entitled AUTOMATIC SUTURING APPARATUS, the entire disclosures of which is herein incorporated by reference. U.S. patent application Ser. No. 12/930,526, filed Jan. 10, 2011, entitled TRANSCORPOREAL DELIVERY SYSTEM AND METHOD FOR VALVULAR REPLACEMENT, the entire disclosure of which is herein incorporated by reference.

FIELD

The field of the invention is an apparatus and method for automatic suturing.

BACKGROUND

One way valves control the flow of blood within the heart. The mitral valve and tricuspid valve are referred to as the atrioventricular valves. The aortic valve and pulmonary valve are referred to as ventriculoarterial valves. Atrioventricular valves control the blood flow between the atria and the ventricle. The left atrioventricular valve is the mitral valve and the right atrioventricular valve is the tricuspid valve. Atrioventricular valves are comprised of an annulus, leaflets, and several chordae tendineae that connect the leaflets to the papillary muscles of their respective ventricles. Mitral valves have two leaflets and tricuspid valves have three leaflets. Ventriculoarterial valves control the blood flow between the ventricles and the two great arteries. The left ventriculoarterial or semilunar valve is the aortic valve and this separates the left ventricle and the aorta. The right ventriculoarterial or semilunar valve is the pulmonary (pulmonic) valve and this separates the right ventricle and the pulmonary artery.

The mitral valve is between the left atrium and the left ventricle of the heart. The mitral valve has two leaflets, an anterior leaflet and a posterior leaflet. The opening mitral valve annulus is a fibrous ring that surrounds the opening of the valve. The mitral valve regulates blood flow from the left atrium to the left ventricle and is a D-shaped annulus with two leaflets that extend into the left ventricle. The chordae tendineae connect the leaflets to the tips of the anterolateral and posteromedial papillary muscles.

The tricuspid valve is between the right atrium and right ventricle. The tricuspid valve regulates blood flow from the right atrium to the right ventricle and is an ovoid shape with three leaflets that extend into the right ventricle. Chordae tendineae extend from the three leaflets and connect to the three papillary muscles.

The pulmonary and aortic valves are referred to as the semilunar valves. Semilunar valves control blood flow between the ventricles and the great arteries. The pulmonary valve is between the right ventricle and the pulmonary artery. The aortic valve is between the left ventricle and the aorta.

In one type of heart valve dysfunction, a damaged, defective, or diseased heart valve may not be able to close properly and allow back flow of blood. This back flow is called regurgitation or incompetence. In this condition, a valve repair or replacement surgery may be performed. When the damage to an atrioventricular valve is less severe, valve repair in this specific situation may be possible. Valve repair involves placement of several sutures in the annulus of the atrioventricular valve and then securing a prosthetic ring in place to reduce the annular dimension and thus reduce the degree of valve incompetence. The prosthetic valve repair ring is constructed of a fixed length of cloth-like material to facilitate fixation of the material to the heart tissue by way of sutures.

In one type of heart valve dysfunction, valve stenosis, the flow area is decreased and blood flow through the valve is decreased. In stenosis, the damage to the valve tissue is often severe and due to calcific deposits or fibrosis. Though valve repair may be performed, valve replacement surgery is most commonly performed for this condition.

A damaged, defective, or diseased heart valve tissue is wholly or partially removed during valve replacement surgery in order to provide a sufficient orifice through which to secure the replacement valve. Replacement of heart valves may utilize prosthetic valves. Biologic valves are constructed out of harvested porcine valve tissue or bovine pericardium. Mechanical valves are constructed out of a metallic alloy. All replacement prosthetic valves have a sewing ring comprised of a cloth-like material to facilitate fixation of the prosthesis to the heart tissue by way of sutures.

In conventional valve replacement, the leaflets are wholly or partially removed and the annulus is circumferentially prepared by the separate insertion of multiple individual sutures. Following preparation of each of these sutures, they are separately inserted into the sewing ring of the prosthetic valve. The prosthetic valve is then lowered into the prepared orifice of the native valve. Then each of the individual sutures is separately tied to secure the valve. Each suture is then individually cut to complete the valve replacement.

The replacement of heart valves requires placement of many sutures. Each pair of suture ends is individually tied. Replacement valves may have a sewing ring that needs to be sewn to the annulus after the defective heart valve is removed. Placement of sutures is a time-consuming process. Curved needles may be used with the sutures to avoid inadvertent penetration of arteries or other structures.

Heart valve replacement surgery may take approximately 4 hours or longer. Historically, in a valve replacement operation, the patient is placed on cardiopulmonary bypass with the heart arrested. The patient is also under anesthesia for a prolonged period of time. A heart valve replacement surgery currently involves the following steps: 1) expose the valve, 2) resect the valve leaflet tissue, 3) place sutures through the annulus of the native tissue, 4) size the prosthesis, 5) place each individual stitch (10-20 pairs) through the sewing ring of the prosthesis, 6) lower the prosthesis and ring into the patient, 7) tie each pair of sutures, and 8) cut each pair of sutures. The number of sutures may range from 12 to over 25 and each is individually tied. A surgeon must be careful to not apply too much or too little tension on the sutures. A heart valve repair surgery currently involves all of the steps above except the valve leaflet tissue is not resected.

Various suturing or fastening apparatus have been developed. These apparatus include but are not limited to the apparatus disclosed in EP139180, U.S. Pat. No. 7,670,370, U.S. Pat. No. 5,417,700, US20040210305, US20060229675, WO2010065912, EP1511429, WO2008048846, WO2008058067, U.S. Pat. No. 6,997,932, and WO1997029694 all of which are incorporated by reference. Many suturing apparatus only place one suture at a time.

Methods or apparatus that can safely shorten the time required to perform replacement of a heart valve will be of benefit to patients and surgeons. In addition, methods and apparatus that will allow heart valve replacement to be done in a minimally invasive manner will also be beneficial. Invasive procedures increase the risk of infection, lengthen recovery time, and are more painful during recovery.

BRIEF SUMMARY

Disclosed herein is an apparatus for suturing a tissue comprising a handle, having a distal end and a proximal end; a suture column, having a distal end and a proximal end, wherein the proximal end is attached to the distal end of the handle; a cylinder ring, wherein the cylinder ring is circumferentially located on the suture column and is capable of moving toward the proximal end of the suture column or distal end of the suture column; a plurality of spokes having a distal end and a proximal end, wherein the proximal end of the spokes is attached to the cylinder ring; one or more triggers present on the handle; a plurality of needles connected to the distal end of the plurality of spokes and operatively connected to one of the one or more triggers; a plurality of sutures threadingly attached to the plurality of needles; and a plurality of tie-bands operatively connected to one of the one or more triggers.

Disclosed herein is an apparatus for suturing a replacement valve to a tissue comprising a handle, having a distal end and a proximal end; a suture column, having a distal end and a proximal end, wherein the proximal end is attached to the distal end of the handle; a cylinder ring, wherein the cylinder ring is circumferentially located on the suture column and is capable of moving toward the proximal end of the suture column or distal end of the suture column; a plurality of spokes having a distal end and a proximal end, wherein the proximal end of the spokes is attached to the cylinder ring; one or more triggers present on the handle; a plurality of needles connected to the distal end of the plurality of spokes and operatively connected to one of the one or more triggers; a plurality of sutures threadingly attached to the plurality of needles; and a plurality of tie-bands operatively connected to one of the one or more triggers. In an embodiment, the cylinder ring moving toward the proximal end of the suture column corresponds with an expanding of the spokes. In an embodiment, the cylinder ring moving toward the distal end of the suture column corresponds with a collapsing of the spokes. In an embodiment, the plurality of spokes comprises radial spokes and vertical spokes. In another embodiment, a plurality of blades is operatively linked to a trigger. In yet another embodiment, the plurality of spokes are on a cylinder. In an embodiment, the plurality of tie-bands surround the sutures and depressing one of the one or more triggers causes compression of the tie-bands around the sutures. In another embodiment, each radial spoke comprises a needle arm, tie-band arm, and blade arm. In an embodiment, each vertical spoke comprises a needle post, tie-band post, and blade post. In another embodiment, the cylinder ring is comprised of one or more pieces. In an embodiment, the apparatus is configured to deploy the plurality of needles at substantially the same time. In another embodiment, a spoke cover is present on the plurality of spokes. In an embodiment, the spoke cover is comprised of fabric. In yet another embodiment, the handle is releasably attached to the suture column.

Disclosed herein is a kit for suturing a valve to a tissue comprising a replacement valve and an apparatus for suturing a replacement valve to a tissue comprising a handle, having a distal end and a proximal end; a suture column, having a distal end and a proximal end, wherein the proximal end is attached to the distal end of the handle; a cylinder ring, wherein the cylinder ring is circumferentially located on the suture column and is capable of moving toward the proximal end of the suture column or distal end of the suture column; a plurality of spokes having a distal end and a proximal end, wherein the proximal end of the spokes is attached to the cylinder ring; one or more triggers present on the handle; a plurality of needles connected to the distal end of the plurality of spokes and operatively connected to one of the one or more triggers; a plurality of sutures threadingly attached to the plurality of needles; and a plurality of tie-bands operatively connected to one of the one or more triggers.

Disclosed herein is a system for suturing a valve to a tissue comprising a replacement valve and an apparatus for suturing a replacement valve to a tissue comprising a handle, having a distal end and a proximal end; a suture column, having a distal end and a proximal end, wherein the proximal end is attached to the distal end of the handle; a cylinder ring, wherein the cylinder ring is circumferentially located on the suture column and is capable of moving toward the proximal end of the suture column or distal end of the suture column; a plurality of spokes having a distal end and a proximal end, wherein the proximal end of the spokes is attached to the cylinder ring; one or more triggers present on the handle; a plurality of needles connected to the distal end of the plurality of spokes and operatively connected to one of the one or more triggers; a plurality of sutures threadingly attached to the plurality of needles; and a plurality of tie-bands operatively connected to one of the one or more triggers.

Disclosed herein is a method for suturing a tissue comprising accessing a tissue of a patient; and suturing the tissue of the patient using an apparatus for suturing a tissue comprising a handle, having a distal end and a proximal end; a suture column, having a distal end and a proximal end, wherein the proximal end is attached to the distal end of the handle; a cylinder ring, wherein the cylinder ring is circumferentially located on the suture column and is capable of moving toward the proximal end of the suture column or distal end of the suture column; a plurality of spokes having a distal end and a proximal end, wherein the proximal end of the spokes is attached to the cylinder ring; one or more triggers present on the handle; a plurality of needles connected to the distal end of the plurality of spokes and operatively connected to one of the one or more triggers; a plurality of sutures threadingly attached to the plurality of needles; and a plurality of tie-bands operatively connected to one of the one or more triggers.

Disclosed herein is a method for suturing a valve to a tissue comprising making an incision in a patient; inserting a replacement valve; attaching the replacement valve to a tissue of the patient using an apparatus for suturing a replacement valve to a tissue comprising a handle, having a distal end and a proximal end; a suture column, having a distal end and a proximal end, wherein the proximal end is attached to the distal end of the handle; a cylinder ring, wherein the cylinder ring is circumferentially located on the suture column and is capable of moving toward the proximal end of the suture column or distal end of the suture column; a plurality of spokes having a distal end and a proximal end, wherein the proximal end of the spokes is attached to the cylinder ring; one or more triggers present on the handle; a plurality of needles connected to the distal end of the plurality of spokes and operatively connected to one of the one or more triggers; a plurality of sutures threadingly attached to the plurality of needles; and a plurality of tie-bands operatively connected to one of the one or more triggers; and closing the incision in the patient. In an embodiment, attaching the replacement valve to a tissue comprises deployment of sutures, securing of sutures, and cutting of sutures. In an embodiment, the handle from the suture column may be detached and attached to the handle to another suture column.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION

The disclosure relates to an apparatus and method for the automatic suturing of valve prostheses during valve replacement or valve repair. It will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, methods, procedures and components have not been described in detail so as not to obscure the embodiments described herein.

The term "replacement valve", when used in this specification and claims, refers to prosthetic valves such as mechanical valves or biological valves such as porcine valves or bovine pericardial valves. In an embodiment, the prosthetic valves may be commercially available.

The term "suture", when used in this specification and claims, may refer 1) to the thread or other material used to join an object to a tissue or to join tissues and 2) to the stitch that is formed using the thread or other material.

Disclosed herein are apparatus, systems, kits and methods for repair and replacement of heart valves using minimally invasive techniques.

Disclosed herein is an automatic suture delivery apparatus that is deployed to attach heart tissue to the sewing ring of an implantable valve and a method to secure a prosthetic device or heart valve implant to tissue using the automatic suture delivery apparatus. Examples of valves that may be sutured to tissue using the apparatus are mitral valves, aortic valves, tricuspid valves, and pulmonic valves. The automatic suturing apparatus may be used upon any type of valve. Also disclosed are systems and kits using the automatic suturing apparatus.

The automatic suturing apparatus may be used upon any tissue, any species, and in any age of patient in need of suturing. In some embodiments, modification or adaptation of the automatic suturing apparatus may be required for a particular use. For example, modifications to the size of the cylinder may be required. In an embodiment, the apparatus may be used on a pediatric patient. In another embodiment, the apparatus may be used on an elderly patient. In an embodiment, the apparatus may be used on a veterinary patient. In various embodiments, the apparatus may be used in the repair of septal defects or for suturing endocardiac patches or baffles. In other embodiments, the apparatus may be used in gynecological surgeries, such as hysterectomies, and in general surgeries such as hernia repair and colon surgery anastomoses. In an embodiment, the apparatus may be used to secure a reinforcement to an any annulus in need thereof.

The apparatus permits the simultaneous fixation of a prosthesis for valve replacement or repair to the annulus or native heart tissue by the automatic placement of multiple sutures, securing the sutures and cutting the sutures by a singular action. Due to the low profile of the automatic suturing apparatus, it is ideally suited for minimally invasive surgical application.

The automatic suturing apparatus may be used for biologic or mechanical prosthetic valvular replacement or for annuloplasty rings used in valve repair. It provides simultaneous delivery of multiple circumferential sutures, securing suture to tissue, and cutting of the suture with one step. In an embodiment, the technique requires the surgeon to expose the valve, remove any necessary pathological leaflet tissue (for replacement), size and seat the prosthesis of choice, and deploy the automatic suturing apparatus. The apparatus delivers multiple sutures, ties the sutures and cuts the sutures, thus completing the valve procedure. The automatic suturing apparatus thus eliminates traditional individual suture placement in the heart annular tissue. Traditional suture placement usually uses 10-12 sutures with 2 needles each. Tying and cutting during traditional suture placement usually takes between 20-40 minutes. The apparatus eliminates placement of each of the suture needles through the sewing ring of the prosthesis as well as tying and cutting each suture. This saves the patient a minimum of 30 minutes, but in some cases up to 60 minutes, of ischemic time during a valvular operation. The automatic suturing apparatus is well-suited for open and minimally invasive valvular operations.

The replacement valve is deployed before securing and stitching. In an embodiment, the valve may be implanted using an apparatus comprising the handle of the automatic suturing apparatus. The handle of the automatic suturing apparatus may be detached and attached to various apparatuses for use in surgery. Alternatively, the apparatus may be used for an annuloplasty, in which a ring is placed around the circumference of the valve.

Figure 1:
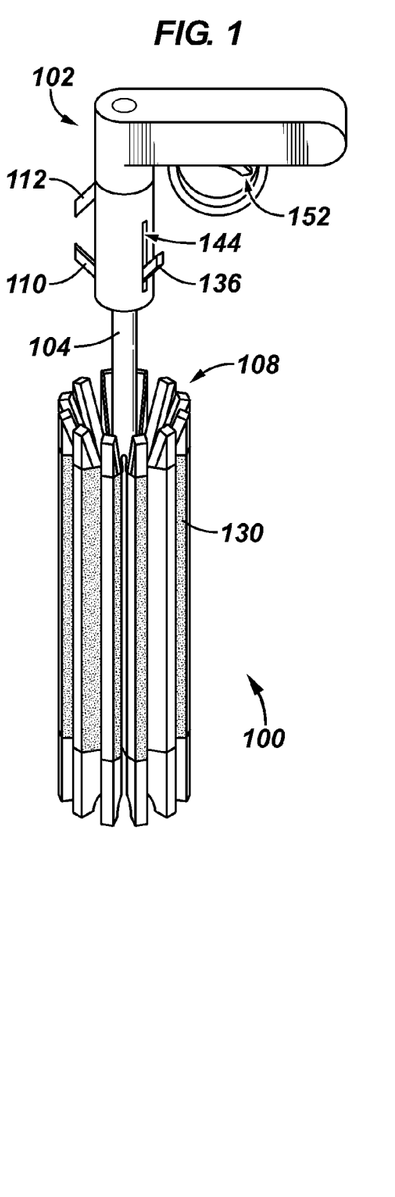
FIG. 1 depicts an automatic suturing apparatus in the compressed orientation.
Figure 2:
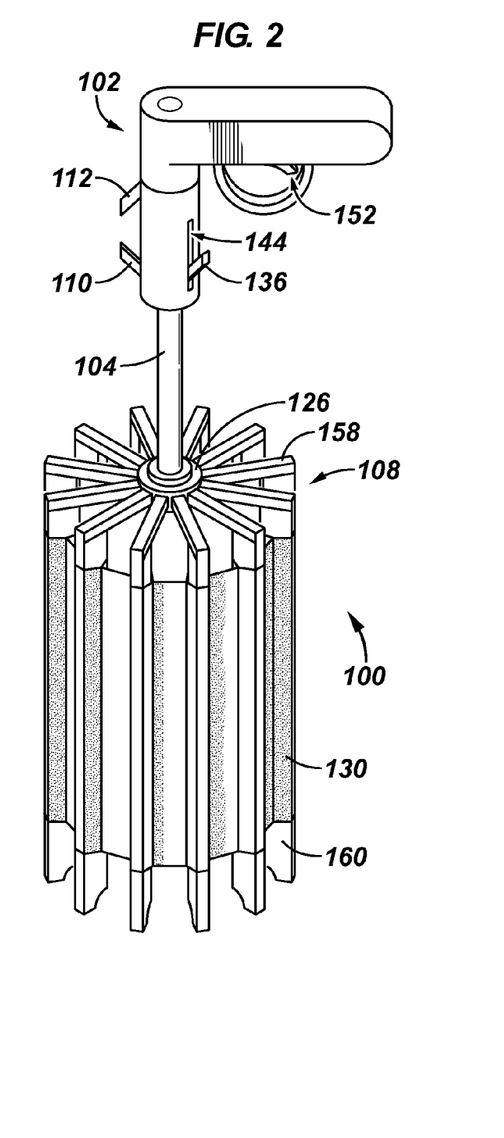
FIG. 2 depicts an automatic suturing apparatus in the expanded orientation.

The automatic suturing apparatus may optionally be compressed (FIG. 1) through a small hole in the chest wall and subsequently expanded (FIG. 2). In an open operation, compression of the automatic suturing apparatus would not be required.

In an embodiment, the automatic suturing apparatus is used according to the following steps: 1) compression; 2) expansion; 3) deployment of sutures; 4) securing of sutures; and 5) cutting of sutures.

A heart valve replacement surgery currently involves the following steps: 1) expose the valve, 2) resect the valve leaflet tissue, 3) place sutures through the annulus of the native tissue, 4) size the prosthesis, 5) place each individual stitch (10-20 pairs) through the sewing ring of the prosthesis, 6) lower the prosthesis and ring into the patient, 7) tie each pair of sutures, and 8) cut each pair of sutures. A heart valve repair surgery currently involves all of the steps above except the valve leaflet tissue is not resected.

FIG. 1 depicts an automatic suturing apparatus 100 in the collapsed orientation.

FIG. 2 depicts an automatic suturing apparatus 100 in the expanded orientation. Activation (pulling up) of suture column trigger 136 causes all three interlocking pieces of the cylinder ring 126 to move in unison, causing the cylinder ring 126 to move toward the proximal end of the suture column 104 and expand the spokes 108.

Figure 3:
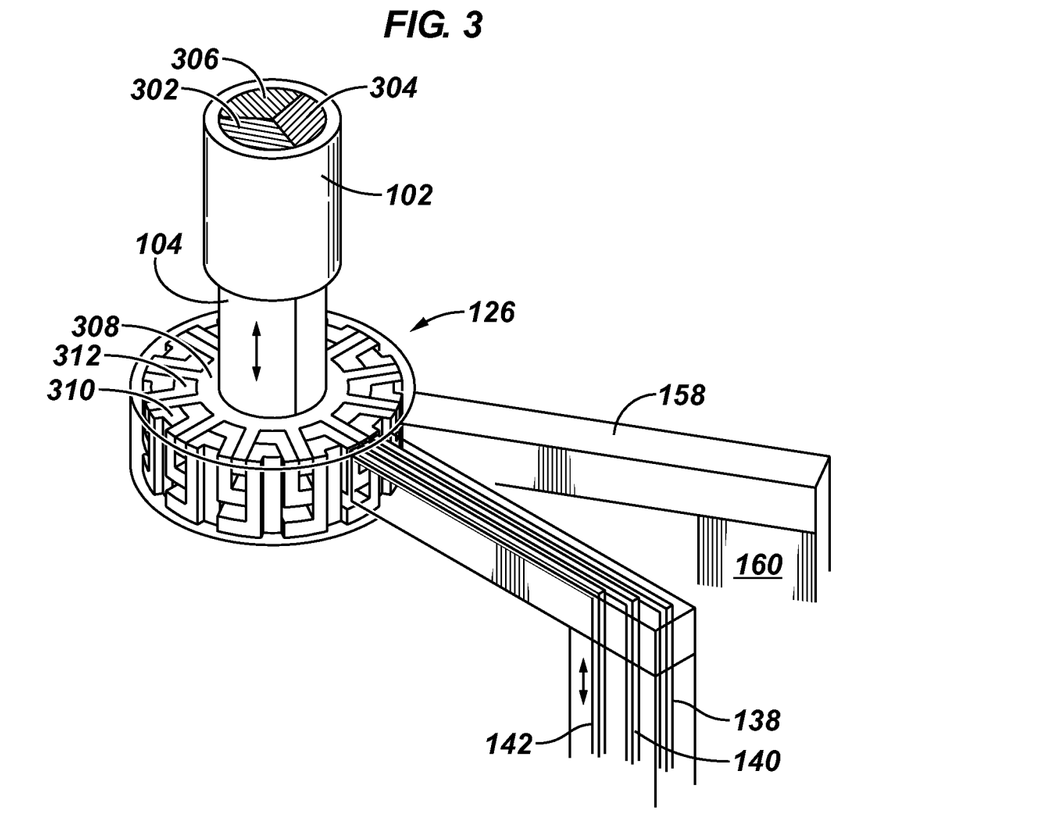
FIG. 3 depicts a view of the suture column and a portion of the cylinder ring of the automatic suturing apparatus.

FIG. 3 depicts a view of the suture column 104 and cylinder ring 126 of the automatic suturing apparatus 100. Activation of needle trigger 110, tie-band trigger 112, or blade trigger 144 (FIG. 2) cause vertical movement of the needle bar 302, tie-band bar 304, or blade bar 306 respectively. The vertical movement of the bars causes movement in the needle interlocking piece 308, tie-band interlocking piece 310, and blade interlocking piece 312.

Figure 4:
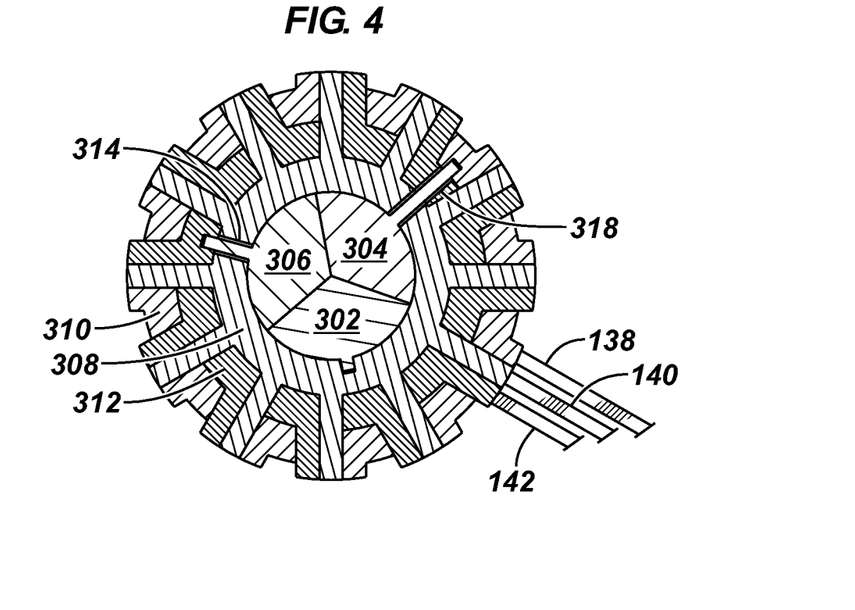
FIG. 4 depicts a cross-sectional view through the cylinder ring and radial spoke.

FIG. 4 depicts a cross-sectional view through the cylinder ring 126 and radial spoke 158. The needle bar 302, tie-band bar 304, and blade bar 306 are attached to the needle interlocking piece 308, tie-band interlocking piece 310, and blade interlocking piece 312 respectively. The needle bar 302 is attached directly to the needle interlocking piece 308. The blade bar 306 goes through the needle interlocking piece slot 314 in the needle interlocking piece 308 to attach directly to the blade interlocking piece 312. The tie-band bar 304 goes through a needle interlocking piece slot 314 in the needle interlocking piece 308 and a blade interlocking piece slot 318 in the blade interlocking piece 312 to attach directly to the tie-band interlocking piece 310.

Figure 5:
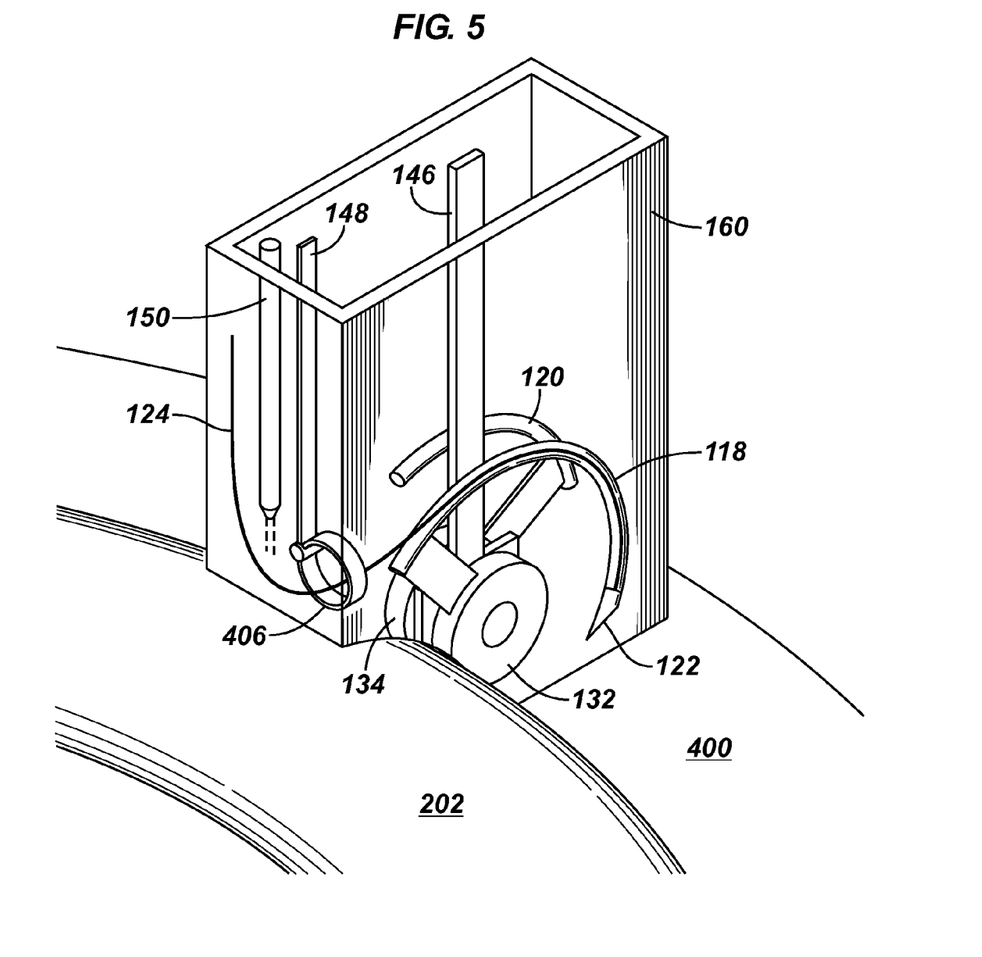
FIG. 5 depicts a view of the needle and tie-band in the resting position.
Figure 9:
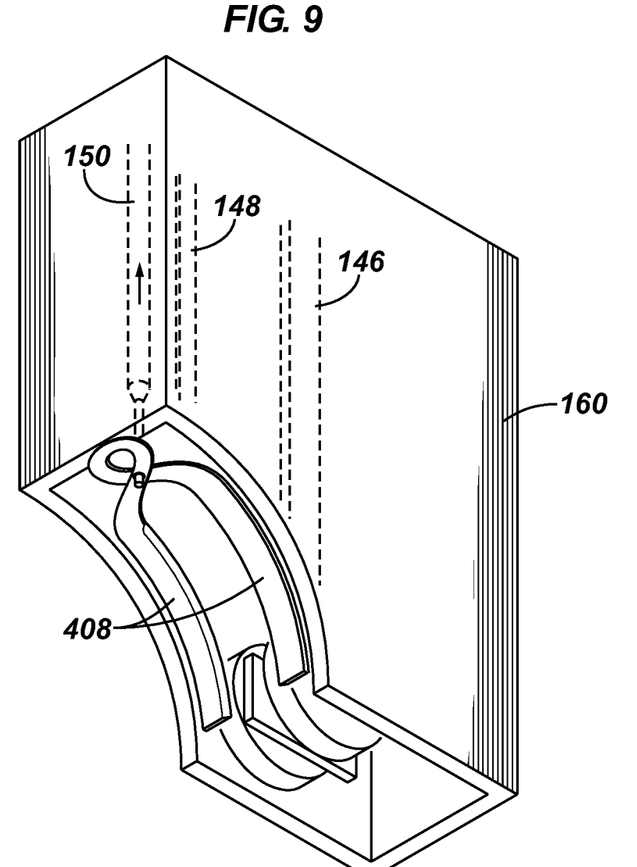
FIG. 9 depicts a view of the blades and blade post within the spoke with the blades in an open conformation.
Figure 10:
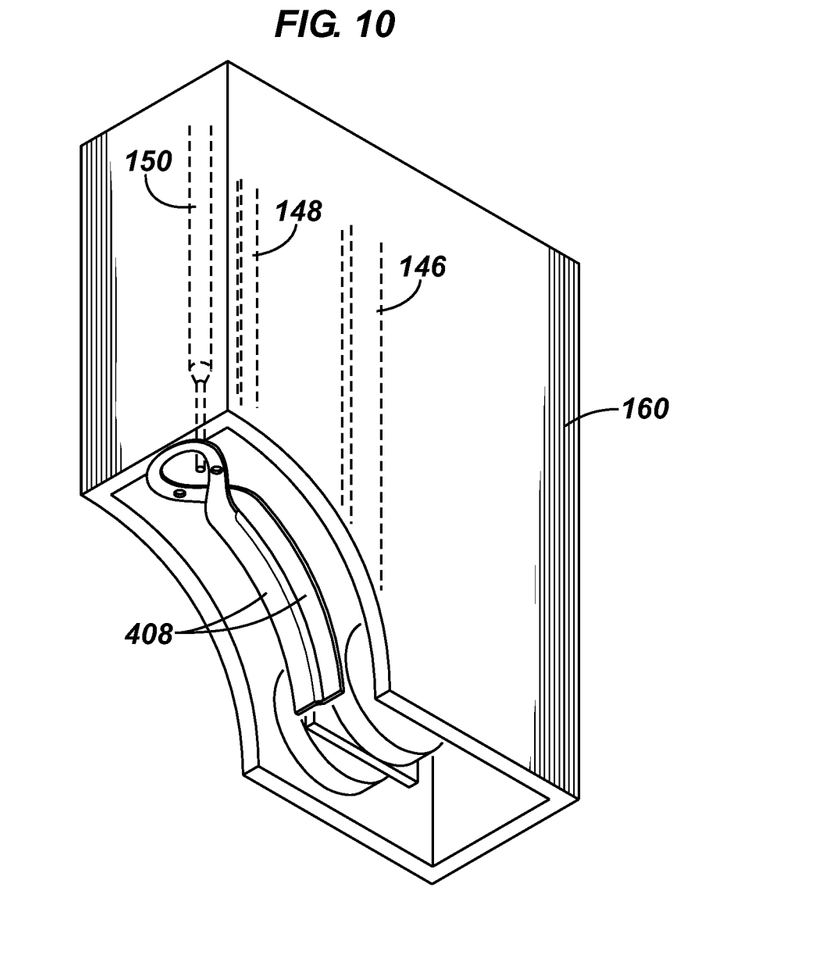
FIG. 10 depicts a view of the blades and blade post within the spoke with the blades in a closed conformation.

FIG. 5 depicts a view of the needle 122 in the resting position and tie-band 406. The position of the leading needle guide 118 and needle capture guide 120 is that prior to the activation of the needle trigger 110. Portions of the blade mechanism are not shown in this figure for the purpose of clarity. The blade mechanism is shown in FIG. 9 and FIG. 10. The vertical spoke 160 rests upon the sewing ring of the replacement valve 202 and the heart tissue 400.

Figure 6:
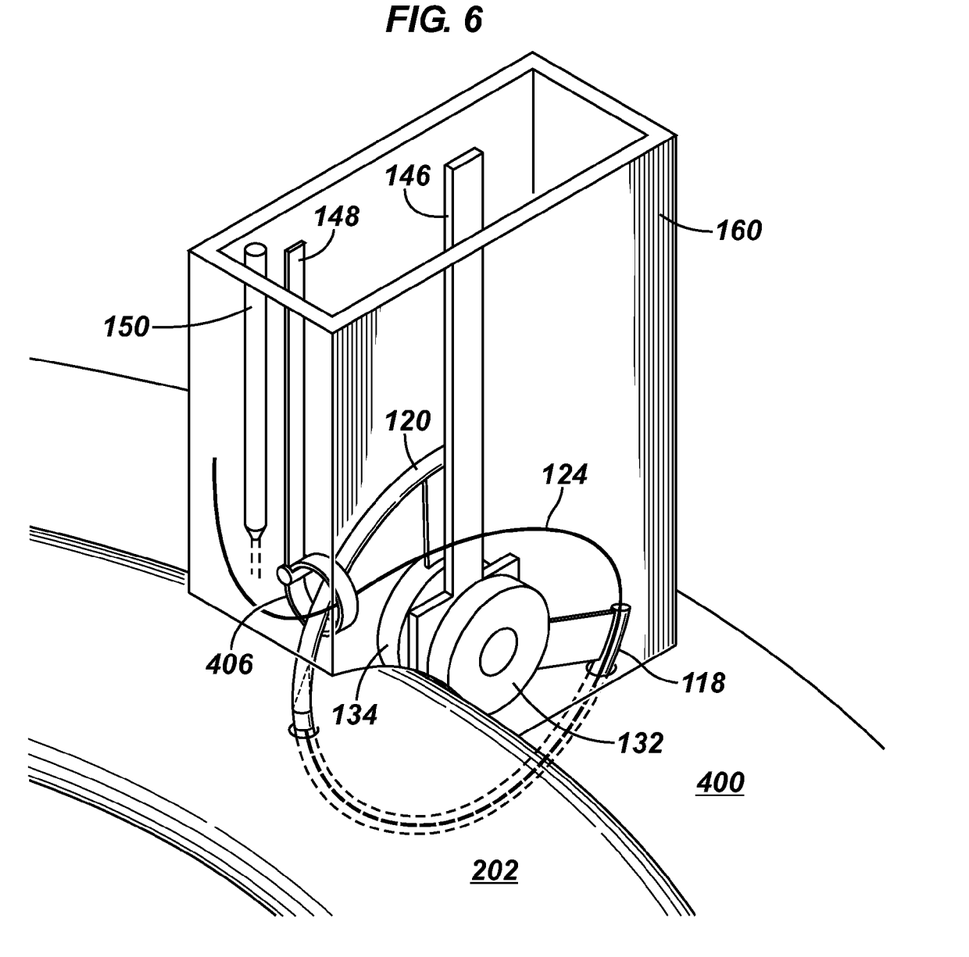
FIG. 6 depicts a view of the needle and tie-band in the position in which the needle is captured by the needle capture guide.

FIG. 6 depicts a view of the needle 122 and tie-band 406 at the position in which the needle 122 is capture by the needle capture guide 120. Portions of the blade mechanism are not shown in this figure for the purpose of clarity. The blade mechanism is shown in FIG. 9 and FIG. 10. The vertical spoke 160 rests upon the sewing ring of the replacement valve 202 and the heart tissue 400.

Figure 7:
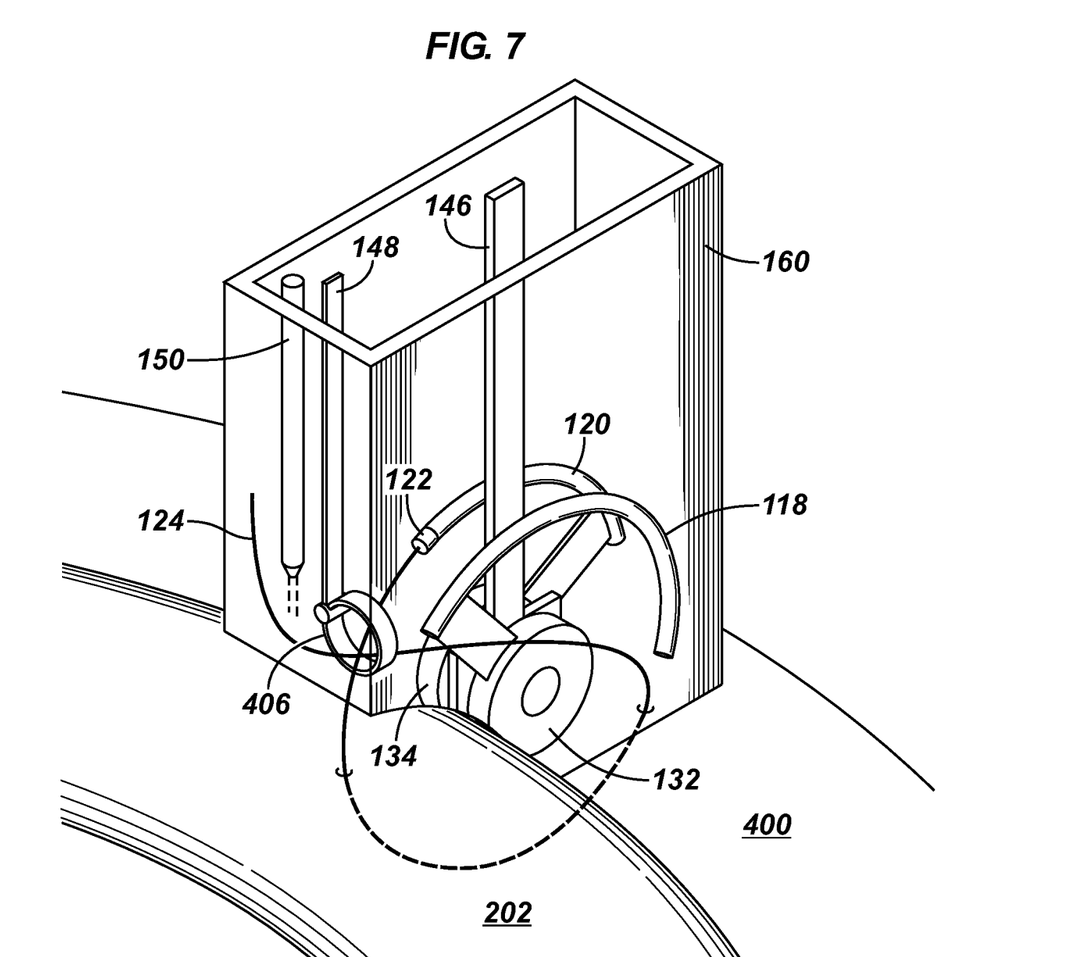
FIG. 7 depicts a view of both ends of the suture present in the tie-band.

FIG. 7 depicts a view of both ends of the suture 124 present in the tie-band 406.

Figure 8:
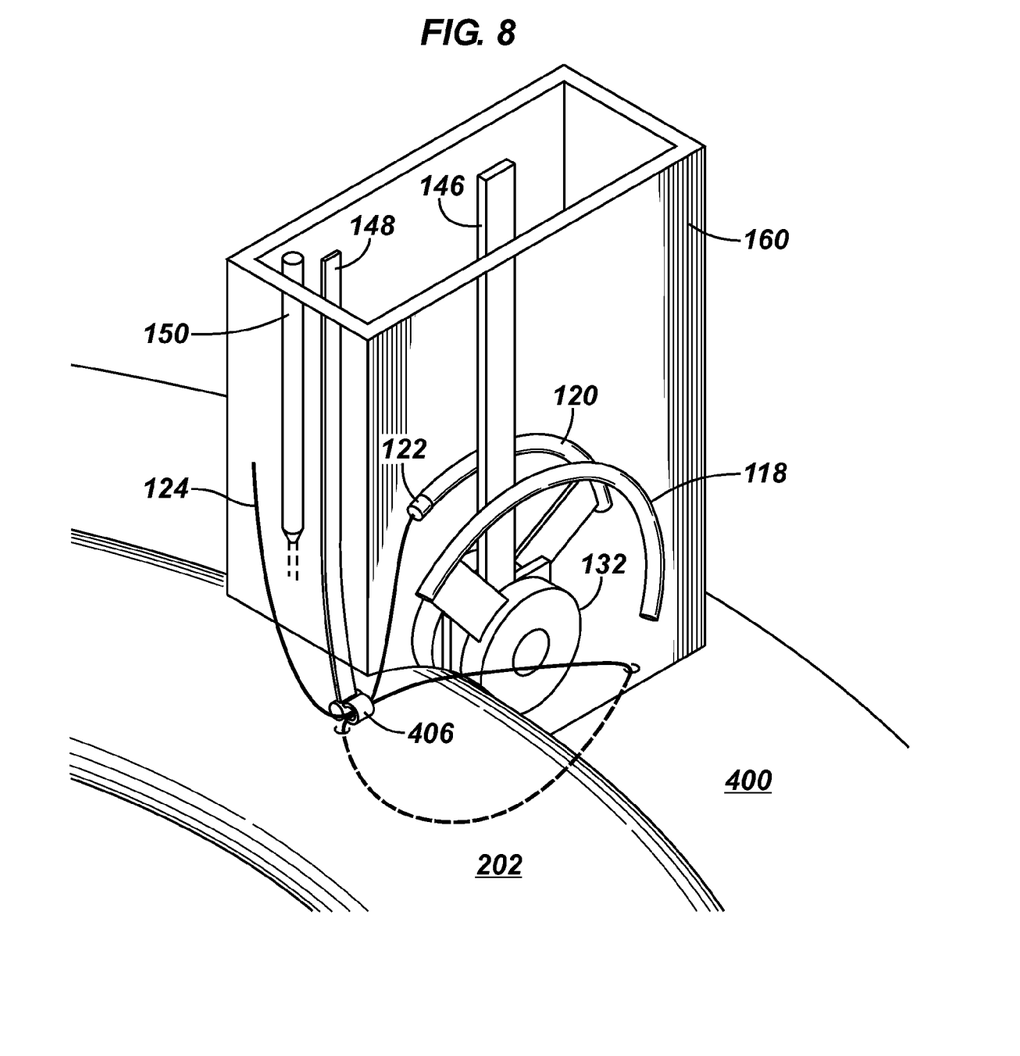
FIG. 8 depicts a view of the tie-band tightening around the ends of the suture.

FIG. 8 depicts a view of the tie-band 406 tightening around the ends of the suture 124.

FIG. 9 depicts a view of the blades 408 and blade post 150 within the vertical spoke 160 with the blades 408 in an open conformation. The majority of the needle mechanism is not shown in this figure for clarity. The needle mechanism is shown in FIG. 5 and FIG. 6.

FIG. 10 depicts a view of the blades 408 and blade post 150 within the spoke vertical spoke 160 with the blades 408 in a closed conformation. The majority of the needle mechanism is not shown in this figure for clarity. The needle mechanism is shown in FIG. 5 and FIG. 6.

Figure 11:
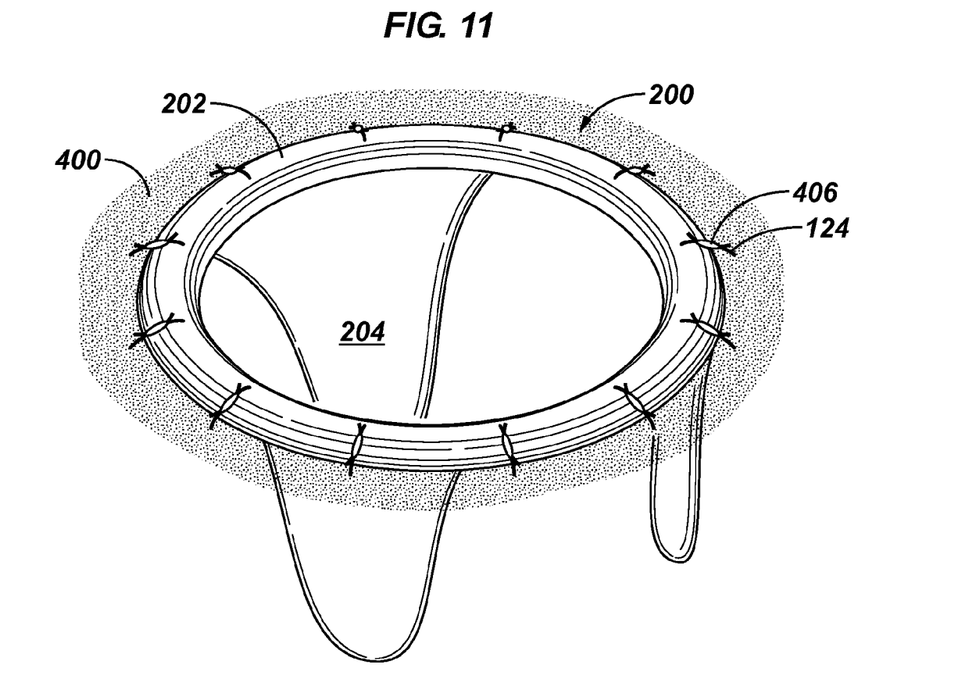
FIG. 11 depicts a perspective view of the sutured and secured mitral valve replacement.

FIG. 11 depicts a perspective view of the sutured and secured mitral valve replacement 200. The sutures 124 with tie-bands 406 adhere the sewing ring of the replacement valve 202 to the heart tissue 400 of the patient.

A heart valve replacement surgery using the automatic suturing apparatus 100 involves the following steps: 1) expose the valve, 2) resect the valve leaflet tissue, 3) size and place the replacement valve in the patient, 4) lower the automatic suturing apparatus 100 and activate the suture column trigger 136 to expand the spokes 108, 5) activate the needle trigger 110 to deploy the needles 122 through the sewing ring of the replacement valve 202, 6) activate tie-band trigger 112 to cause the tie-bands 406 to secure the sutures, and 7) activate the blade trigger 152 to cause the blades 408 to cut the sutures 124. In an embodiment, the cylinder 106 from which the sutures 124 were deployed may be removed and another cylinder 106 with sutures 124 loaded may be attached to the handle 102. In an embodiment, additional sutures may be placed in the sewing ring of the prosthesis 202 using the cylinder 106 with loaded sutures 124.

In an embodiment, the handle 102 may be removably attached to a valve placement apparatus or a cylinder of an automatic suturing apparatus. In an embodiment, a replacement cylinder may be attached to the handle 102 after suturing has occurred to provide additional sutures. In an embodiment, all or a portion of the cylinder 106 may optionally be covered with a removable or retractable cover prior to suturing. In an embodiment, the needles 122 may be covered with a removable or retractable cover prior to suturing.

The automatic suturing apparatus 100 may be used to secure a replacement valve for any type of valve. In an example, the valve is a mitral valve. In another example, the valve is an aortic valve.

In an embodiment, the automatic suturing apparatus 100 comprises four triggers. Each of the four triggers causes an action. The suture column trigger 136 causes the cylinder 106 to expand or compress. Suture column trigger 136 actuates all 3 interlocking pieces of the cylinder ring 126 causing cylinder 106 to move toward the proximal end of the suture column 104. The needle trigger 110 causes the needles 122 to deploy through the sewing ring of the replacement valve 202. The vertical spokes 160 rest on a replacement mitral valve 200 or replacement aortic valve 206. The vertical spokes 160 of the automatic suturing apparatus 100 partially overhang the sewing ring of the replacement mitral valve 202. The tie-band trigger 112 causes the tie-bands 406 to tighten on the sutures 124. The blade trigger 152 causes the blades 408 to cut the sutures 124 by retracting the blade post 150 and allowing the spring-loaded blades 408 to come together, severing the sutures 124. In an embodiment, the blades 408 are pre-coiled spring-loaded blades. Any trigger mechanism that would function to activate the various portions of the apparatus may be used in the apparatus. The suture column trigger 136 are located in a suture column trigger slot 144.

The suture column 104 may be metallic and hollow. The needle arm 138, tie-band arm 140, and blade arms 142 within the spokes are activated by triggers that work on a sliding bar. In an embodiment, the sliding bar is hinged for blade trigger 152. The vertical up and down motion actuates a portion of the cylinder ring 126. Suture column trigger 136 moves all portions of the cylinder ring 126 in unison, while the needle trigger 110, tie-band trigger 112, and blade trigger 152 move respective sub-portions of the cylinder ring 126 for the specific function outlined.

For example, the needle interlocking piece 308 vertical up and down motion is triggered by the needle trigger 110. The motion of needle interlocking piece 308 actuates the needle arm 138 within the radial spoke 158 to move it in a similar vertical motion. The motion of needle arm 138 is translated down needle post 146 and deploys the leading needle guide 118 with needle 122 and the needle capture guide 120.

The cylinder ring 126 may contain three separate pieces that may be activated together by the suture column trigger 136 to raise the entire cylinder ring 126 or move portions of the cylinder ring 126 individually by the needle trigger 110, tie-band trigger 112, or blade trigger 152 to deploy the needles 122, tie-bands 406, or blades 408 respectively. In an embodiment, the portions of the cylinder ring 126 interlock. Slots in the suture column 104 allow for interaction of the bars with the respective interlocking piece of the cylinder ring 126 for the needles 122, tie-bands 406, or blades 408. In an embodiment, the three separate pieces of the cylinder ring 126 may be concentric circles.

Each bar may be solidly attached to the respective interlocking piece. (FIG. 3 and FIG. 4). In an embodiment, the cylinder ring 126 is comprised of three interlocking pieces, the needle interlocking piece 308, tie-band interlocking piece 310, and blade interlocking piece 312, that are separately activated by a given trigger but interlock so that the entire cylinder ring 126 may move in synchrony as a single ring. The cylinder ring 126 is composed of three interlocking pieces with twelve segments each. Twelve segments are located on the needle interlocking piece 308 and are is related to the needle arm 138, twelve are located on one tie-band interlocking piece 310 of the cylinder ring 126 and related to the tie-band arm 140, and twelve are located on the blade interlocking piece 312 of the cylinder ring 126 and related to the blade arm 142. All twelve segments are interrelated and move when the trigger for the needle arm 138, tie-band arm 140, and blade arm 142 is depressed. In an embodiment, there are slots in the handle 102 and suture column 104 to allow movement of the triggers. Movement of the triggers causes movement of the sliding bars and the interlocking pieces of the cylinder ring 126.

Each trigger may be solidly attached to the respective interlocking piece. (FIG. 3 and FIG. 4). The needle interlocking piece 308 vertical up and down motion is triggered by the needle trigger 110. In an embodiment, the needle bar 302 is directly solidly attached to the innermost interlocking piece, the needle interlocking piece 308. The blade bar 306 is attached to the next interlocking piece, the blade interlocking piece 312, through a needle interlocking piece slot 314 in the needle interlocking piece 308. The tie-band bar 304 is attached to the outermost interlocking piece, the tie-band interlocking piece 310, through a needle interlocking piece slot 314 in the needle interlocking piece 308 and a blade interlocking piece slot 318 in the blade interlocking piece 312. In an embodiment, the slots 314 and 318 are at least 10-15 mm in height to allow for motion between the interlocking pieces 308, 310, and 312. The motion of needle interlocking piece 308 actuates the needle arm 138 within the radial spoke 158 to move needle arm 138 in a similar vertical motion. The motion of needle arm 138 is translated down needle post 146 and deploys the leading needle guide 118 with needle 122 and the needle capture guide 120. Any structure of cylinder ring that would transfer the activation of the trigger to the individual arms may be used in the apparatus.

Each radial spoke 158 comprises a needle arm 138, tie-band arm 140, and blade arm 142. Each vertical spoke 160 comprises a needle post 146, tie-band post 148, and blade post 150. In an embodiment, the arms and posts may be secured to the interior wall of the radial spoke 158 or vertical spoke 160 with a securing structure. In an embodiment, the arms and posts do not touch the interior walls of the radial spoke 158 or vertical spokes 160. In an embodiment, the arms and posts may be two separate structures. In an embodiment, the arms and posts may be two parts of one structure.

In an embodiment, only 0.2 to 1.0 cm of motion in a vertical direction is required to activate the needles 122, tie-bands 406, or blades 408. In an embodiment, the motion is 0.5 cm. The downward motion exerted on the needle arm 138 causes the needle post 146 to move downward and deploy the needles 122. The downward motion exerted on the tie-band arm 140 causes the tie-band post 148 to move downward and the tie-band 406 to secure the sutures 124 and detach. The upward movement of the blade arm 142 causes the blade post 150 to move upward and allows the blades 408 to come together to cut the sutures 124.

The cylinder 106 has multiple leading needle guides 118, needle capture guides 120, and needles 122 situated around its circumference. The suture column 104 is located proximal to and in the center of the cylinder 106.

The needle 122 is attached to the suture 124 and is present in the leading needle guide 118. In an embodiment, the suture 124 is attached to the end of the needle 122. (FIG. 5) In an embodiment, the suture 124 exists on the outside of the leading needle guide 118 through the end opposite where the needle 122 is located. In an embodiment, the leading needle guide 118 may be solid except for the section where is the needle 122 is located. The other end of the suture 124 is threaded through the tie-band 406. In an embodiment, to section of the leading needle guide 118 may be hollow with the suture 124 attached to the needle 122. In an embodiment, the suture 124 may exit through a hole in the leading needle guide 118.

As the needle 122 and suture 124 are deployed, they travel in a circle through the heart tissue 400 and the sewing ring of the mitral valve replacement 202 and into the needle capture guide 120 as the needle exits the sewing ring 202. (FIG. 6)

During retraction of the needle 122, the needle 122 and suture 124 are pulled through the tie-band 406 as the needle 122 continues to travel in a circle. (FIG. 7) The quick release mechanism of the leading needle guide 118 permits tension-free removal of the needle 122 and freedom of the suture 124. Any type of needle mechanism that would function to place a suture in a sewing ring may be used in the apparatus.

In an embodiment, the deployment of the sutures 124 by the leading needle guide 118 occurs at an angle between 170-degrees to 280-degrees. In an embodiment, the deployment of the sutures 124 occurs at between 180-degrees to 270-degrees.

In an example, the vertical up and down motion of the tie-band interlocking piece 310 is activated by the tie-band trigger 112. The motion of tie-band interlocking piece 310 actuates the tie-band arm 140 within the radial spoke 158 to move tie-band arm 140 in a similar vertical motion. The motion of tie-band arm 140 is translated down tie-band post 148 and activates the tightening of the tie-band 406. As the tie-band 406 tightens around the sutures 124, the tie-band 406 detaches from the tie-band post 148. (FIG. 8) Any type of structure or method that would secure the ends of the sutures 124 may be used in the apparatus.

In another example, the vertical up and down motion of the blade interlocking piece 312 is activated by the blade trigger 152. The motion of blade interlocking piece 312 actuates the blade arm 142 within the radial spoke 158 to move the blade arm 142 in a similar vertical motion. The upward motion of blade arm 142 is translated through blade post 150 and activates release of the blades 408. The blades 408 are spring-loaded and set in an open position until activated by blade trigger 152. (FIG. 9) The activation of the blade trigger 152 pulls up the blade arm 142 and blade post 150 to release the spring. (FIG. 10) The release of the spring causes the blades 408 to close, thus cutting the suture 124. (FIG. 10) The sutures 124 are held taught until severing because of the resting position of needles 122 following activation of needle trigger 110. Any structure or method of severing the suture ends may be used in the apparatus.

In an embodiment, the leading needle guide 118 and the needle capture guide 120 are located on two separate flywheels, the leading needle guide flywheel 132 and the needle capture guide flywheel 134 respectively. (FIG. 5) The downward motion of the needle post 146 moves the needle capture guide flywheel 134 in a counter-clockwise direction and the leading needle guide flywheel 132 in a clockwise direction. The flywheels, the leading needle guide flywheel 132 and the needle capture guide flywheel 134, are separate and parallel to each other. The leading needle guide flywheel 132 and the needle capture guide flywheel 134 may be offset approximately 10 degrees to avoid crossing the needle post 146. The connections may be hinged and slightly angled to permit semicircular action of each respective connection to the flywheel. An upward motion of needle trigger 110 causes an upward motion of the needle arm 138 and needle post 146, resulting in retraction of the needle capture guide 118 and leading needle guide 120.

In an embodiment, the needle capture guide 120 and leading needle guide 118 meet at a point above the sewing ring of the replacement valve 202. The needle post 146 is allowed downward movement between the leading needle guide flywheel 132 and the needle capture guide flywheel 134. The needle capture guide 120, when deployed, travels through the tie-band 406. (FIG. 6) The leading needle guide 118 meets the needle capture guide 120 and the needle 122 becomes lodged in the needle capture guide 120. With an upward motion of the needle trigger 110, the needle capture guide 120 is pulled back through the tie-band 406, bringing the needle 122 and suture 124 with it. In an embodiment, the needle 122 is shaped like an arrowhead with the suture 124 attached to the rear portion of the arrowhead. In an embodiment, the suture 124 is on the outside of the leading needle guide 118. The other end of the suture 124 is already present in the tie-band 406 as the suture 124 travels through the tie-band 406 with the leading needle guide 118 and needle 122. (FIG. 7) In an embodiment, the suture may be attached to the interior of the vertical spoke 160.

The tie-band trigger 112 activates the tie-band post 148. As the tie-band trigger 112 is activated, it causes the tie-band post 148 to move downward. The tie-band 406 has pre-set perforated edges and tightens and narrows on the suture 124 as the tightening tension is reached. (FIG. 8) The tie-band 406 then detaches from the tie-band post 148.

In an embodiment, each suture 124 goes through and is secured by a tie-band 406. In an embodiment, the tie-band 406 is a metallic alloy or polymer and is similar to a zip tie. The tie-band 406 surrounds the two ends of the suture, which are threaded through the tie-band 406. (FIG. 7) The tie-band 406 is secured with a tie-band post 148 that pulls the tail of the tie-band 406 to a taut position and is then detached. (FIG. 8) The tie-band post 148 and tie-band 406 may be perforated for easy detachment.

In an embodiment, the method of securing the sutures is similar to a finger trap. In this embodiment, the suture threads are pulled through a corrugated internal tube with string. The corrugated internal tube is secured tight by pulling the suture threads. The tube stays in place as the suture threads are pulled in opposite directions and are secured with corrugation.

In an alternate embodiment, the tie-band has a wide band, corrugated edges, and grooves on the inside. The tie-band is compressed through the action of pulling the sutures. The end position is similar to a full conic (open on both ends, tight in the middle). The ends of the conic have reverse-facing angled surfaces to prevent the thread from pulling loose.

Blade trigger 152 may be located in the handle 102. Activation of the blade trigger 152 pulls up the blade arm 142 in the radial spoke 158, thus pulling up the blade post 150 in the vertical spoke 160. (FIG. 9) The base of the blade post 150 is pulled up, releasing the blades 408 and severing the sutures 124. (FIG. 10) In an embodiment, the blades 408 are pre-coiled spring-loaded blades.

In another embodiment, a tie-band post has blades attached to the post in a mid-line position. As the tie-band post moves downward, the blades are held in the open position. Once the tie-band is released, the blades return to the mid-line position, thus cutting the suture.

In an embodiment, the automatic suturing apparatus 100 may have the following dimensions. The cylinder 106 may have a height of 5-10 cm containing between 4 and 16 suture locations. In an embodiment, the cylinder 106 has 12 suture locations. When compressed, the cylinder may be 25% of the uncompressed diameter. The automatic suturing apparatus 100 may rest on the exterior of the sewing ring of the replacement valve 202 flush with the valve annulus or heart tissue 400. In an embodiment, the expanded diameter of the cylinder 106 ranges from 15-40 mm with a 5 mm diameter variance (flex). Replacement mitral valves 200 range from 25 to 33 mm and vary by 2 mm. In an embodiment, a replacement mitral valve 200 may be 25, 27, 29, 31, or 33 mm. Replacement aortic valves may range from 19 to 29 mm. In an embodiment, a replacement aortic valve may be 17, 19, 21, 23, 25, 27, or 29 mm. In an embodiment, annuloplasty rings are available in 24, 26, 28, 30, 32, 34, 36, 38, or 40 mm sizes.

In an embodiment, three different sizes of cylinders 106 may be available for the automatic suturing apparatus 100 for use with various sizes of valve replacements. In an embodiment, the available column sizes are 21, 25, and 31 mm. The adjustability of the cylinders allows for use with a variety of sizes of replacement valve. The 2-3 mm adjustability allows for fine adjustment by the operator to achieve an optimal fit with the replacement valve.

In an embodiment, the diameter of the cylinder 106 is adjustable. In an embodiment, the diameter of the cylinder 106 may be adjusted by a dial. Expansion of the cylinder may be similar to the expansion of an umbrella. In an embodiment, expansion occurs by a rotating shaft with a stopper-like chamfer having mechanical stops. In an embodiment, a spring-loaded cylinder will provide tension inward on a cylinder.

In an embodiment, the vertical spokes 160 are covered with a spoke cover 130 that may be a pliable fabric that is capable of expanding and contracting. In an embodiment, the fabric is nylon or a nylon-like fabric. In an embodiment, the spoke cover 130 may be attached to the vertical spokes 160. In an embodiment, the spoke cover 130 may be attached to the radial spokes 158.

The suture column 104 may be a metallic alloy tube with 3 trigger bars or lines that are actuated by 4 triggers with vertical up and down motion. In an embodiment, there are 4-16 radial spokes 158 and 4-16 vertical spokes 160. In an embodiment, there are 12 radial spokes 158 and 4-16 vertical spokes 160. The radial spokes 158 and 4-16 vertical spokes 160 may be constructed of a malleable polypropylene or plastic suitable for gas sterilization. A ring may be present at the corner where the radial spoke 158 and vertical spoke 160 meet.

Various Mechanisms for Deployment of Sutures:

In an embodiment (FIG. 5), the automatic suturing apparatus 100 sits directly on top of the sewing ring of the replacement valve 202 with an overhang on the tissue 400. The orientation of the automatic suturing apparatus 100 is at 90-degrees to the sewing ring 202. In an embodiment, the stitching direction is from the outside of the sewing ring 202 to the inside of the sewing ring. In another embodiment, the stitching direction is substantially parallel to the edge of the sewing ring of the replacement mitral valve. In an embodiment, the base of the cylinder 106 is flush with the tissue 400 by approximately 2 mm. The lip of the cylinder 106 is between 5 mm to 10 mm. The cylinder 106 fits around the sewing ring of the replacement valve 202. The automatic suturing apparatus 100 is deployed in a minimally invasive manner in that it can be inserted in an incision of approximately 6-10 centimeters because the spokes 108 are capable of collapsing.

In an embodiment, the automatic suturing apparatus may sit directly on top of the sewing ring of the prosthesis without an overhang on the tissue. The sutures are deployed directly through the sewing ring. The leading needle guide and needle capture guide are deployed and meet within the tissue below the sewing ring to transfer the needle and suture.

The automatic suturing apparatus may be used in different orientations. The automatic suturing apparatus may be used in a vertical direction with the thin direction of the sewing ring perpendicular to the tissue opening. Alternatively, the automatic suturing apparatus may be used in a horizontal direction with the sewing ring parallel to the tissue opening.

In an embodiment, the suturing may occur in four steps: an un-actuated resting position, needle deployment, needle retraction, and the final position of the needle.

There are at least four embodiments of a needle housing mechanism that may be utilized. The embodiments are: A) two nested curved tubes with the needle nested internally; B) two opposed curved tubes with the needle nested internally; C) a single curved tube with the needle nested internally; and D) a single needle attached to suture.

Embodiment A of a needle mechanism is two nested curved tubes with the needle nested internally. The tubes may be in various orientations. The orientation may be approximately 180-degrees or alternatively approximately 270-degrees.

In embodiment A, there are an internal tube A, external tube B, and a needle within internal tube A. This embodiment is similar to a cat claw. Internal tube A and external tube B span approximately 180-degrees. A tie-band is located at the tail end of the needle in a pre-loaded system, with the suture threaded through the inside of the tie-band. The tail of the internal tube may house a spring or circular translation pulley mechanism to drive the interior tube. The spring or circular translational pulley mechanism may be expanded (released) with the shaft from an actuator. The internal tube A fires through the tissue or sewing ring (depending on whether the automatic suturing apparatus overhangs the tissue) and carries with it a needle attached to the suture. The needle is directional and moves in a positive direction. The internal tube A stops when its end reaches the tip of the external tube B that possesses a small tab or notch and alignment is maintained. The internal tube A is retracted with the needle and the suture is released from the needle tip as the needle capture guide retracts with the needle tip and suture. The needle is actuated in the 180-degree position with the head of the needle through the tie-band. Upon completion, internal tube A and external tube B are near the starting position and the needle is contained in external tube B. The suture thread has created a loop through the tie-band.

Embodiment B is two opposed curved tubes with the needle nested internally. The tubes may be in various orientations. The orientation may be approximately 180-degrees or alternatively approximately 270-degrees. The flywheels may be offset to avoid crossing with a needle post.

In embodiment B, there are two opposed tubes that are located at approximately 90-degrees turns and a needle housed inside one the tubes. This embodiment is similar to an insect mandible. A tie-band that is larger than the tubes is located at tail of the needle. A spring is located between the tails of the tubes. The tubes are triggered by the release of the spring through the pulling of an actuating shaft. The needle travels in the appropriate direction within one tube. Each tube allows unidirectional motion of the needle. One tube fires in the positive 90-degree direction, while the other tube fires in the 90-degree direction. After traveling through the first tube, the needle protrudes from the first tube and is captured by the second tube. Both tubes are retracted with string and the needle is drawn up by the other tube. The suture is through the entire circle and the needle is extracted with one of the tubes.

Embodiment C is a single curved tube with the needle nested internally. The tubes may be in various orientations. The orientation may be approximately 180-degrees or alternatively approximately 270-degrees.

In embodiment C, one hollow tube contains the unidirectional needle. A tie-band is located at the tail of the hollow tube. The tube is fired with a spring that is released by an actuating shaft. The needle travels with the hollow tube with the head of the needle stopping where the original tail and spring were located. In an alternate embodiment, a tube simply houses a needle but does not rotate.

Embodiment D is a single needle attached to a suture. The tubes may be in various orientations. The orientation may be approximately 180-degrees or alternatively approximately 270-degrees. The suture is of fixed length so that during securing, there is a relative amount of tension.

In embodiment D, using a spring is used to fire a needle through a sewing ring. A tie-band is located at the original tail of the needle. The spring would provide enough force to fire the needle through a 360-degree rotation.

For embodiments A-D, the arc of the needle may be flat (parallel to stitching ring) or vertical (opening of C around the thin dimension of stitching ring). Alternatively, the needle may travel from a vertical portion of cylinder (annulus) to the flat portion (on stitching ring), resulting in only the exposed step being stitched. In an embodiment, the sutures are secured as a running stitch instead of with the use of a tie-band.

Alternatively, a magnetic drive may be used as the drive mechanism for a needle instead of a spring. When a magnetic drive is used as the drive mechanism, the tip of the needle will have a magnetic property. In an embodiment, a disk with a magnetic property drives the needle through the tissue in a rotating fashion. The disk is actuated by either a string with a spool (rotating the axis of rotation) or a small electric motor. The spinning disk may or may not require shielding. If shielding is required, the magnetic property of the spinning disk is shielded so to not interfere with other activity. In an embodiment, the magnet is located in the outside lip of the cylinder. The magnet is rotated around the ring up and down to control the small needle to do the same.

Various Mechanisms for Cutting:

In an embodiment, an actuating trigger may be present on the automatic suturing apparatus. The blades 408 are similar to a bear trap. A trigger is may be pulled that secures breaks off the tie-band 406.

An alternate actuating trigger puts the blades in position and when the trigger is retracted, the blades close, therefore cutting the sutures.

In an alternate embodiment, there is a rotating blade on the inside of cylinder. The rotating blade is driven by an electric motor, magnet, or pulled with string. When the rotating blade is rotated around the stitching ring, the sutures are cut.

The automatic suturing apparatus 100 comprises an umbrella-like structure having a cylinder 106. (FIG. 1 and FIG. 2) Radial spokes 158 are attached to a cylinder ring 126 that surrounds a suture column 104 circumferentially. When the spokes 108 are folded, the cylinder ring 126 is at the distal end of the suture column 104. (FIG. 1) The folded spokes 108 are attached to the cylinder ring 126. As the cylinder ring 126 slides up the suture column 104, the spokes 108 deploy like an umbrella. (FIG. 2) The cylinder ring 126 actuates vertically on the suture column 104. The circumference of the cylinder 106 increases to match the circumference of the replacement valve 200. Needles 122 and sutures 124 are present at the distal end of the spokes 108. Each needle 122 is attached to a length of suture 124. The needle 122 and suture 124 go through the tissue 400 and sewing ring of the replacement valve 202. The suture 124 follows the needle 122 in a predetermined arc that stops immediately adjacent to the starting position. After deployment of the needles 122, the suture 124 has passed through the sewing ring 202 and tie-band 406. (FIG. 7 and FIG. 8) The tie-band 406 detaches from the tie-band post 148 and acts to hold the suture 124 in place. The blades 408 then sever the sutures 124 (FIG. 9 and FIG. 10).

In an embodiment, the tie-bands 406 are cylindrical in shape with the interior of the cylinder 106 comprised of corrugated titanium or a non-reactive metallic alloy. The tie-bands 406 may be substantially parallel to the sewing ring of the replacement valve 202. After activation of the tie band trigger 112, the tie-bands 406 hold the sutures 124 in place. Tie-band arms 140 and tie band posts 148 are present in each of the radial spoke 158 and vertical spoke 160 respectively. By tightening the tie-band 406, the suture 124 is secured because the compressed tie-band 406 prevents removal or loosening of the suture 124.

The spokes 108 allow for collapsibility. Once opened, the needles 122 may be deployed by way of needle trigger 110 to suture the sewing ring of replacement mitral valve 202 to the heart tissue 400. After completion of suture 124 deployment, tightening of tie-bands 406 (similar to a typical tie-band but with the use of a finger trap mechanism to assure security of the suture), is activated by depression of tie-band trigger 112. The sutures 124 are cut by squeezing the blade trigger 152 to cause the blade post 150 to be pulled up and allow the blades 408 to come together and sever the suture 124. A sutured and secured replacement valve 200 is shown in FIG. 11.

Any examples included herein are to demonstrate preferred embodiments of the present disclosure. It should be appreciated by those of skill in the art that the techniques disclosed in the examples represent techniques discovered by the inventors to function well and thus can be considered to constitute preferred modes for its practice. However, those of skill in the art should, in light of the present disclosure, appreciate that many changes can be made in the specific embodiments which are disclosed and still obtain a like or similar result without departing from the spirit or scope of the disclosure. Any examples are offered by way of illustration and not by way of limitation.

Variations and modifications to the preferred embodiments of the invention described herein will be apparent to those skilled in the art. It is intended that such variations and modifications may be made without departing from the scope of the invention and without diminishing its attendant advantages.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An apparatus for suturing a tissue comprising
   a handle;
   one or more triggers on the handle,
   a suture column, having at least two ends, wherein one end is attached to the handle;
   a cylinder ring, wherein the cylinder ring is capable of sliding on the suture column;
   a plurality of spokes attached to the cylinder ring;
   a plurality of needles connected to the plurality of spokes;
   a plurality of sutures attached to the plurality of needles; and
   a plurality of tie-bands, wherein one of the plurality of sutures is surrounded by one of the plurality of tie-bands.

2. The apparatus of claim 1 wherein the apparatus is an apparatus for suturing a replacement valve to a tissue.

3. The apparatus of claim 1, wherein the cylinder ring moving toward the handle on the suture column corresponds with an expanding of the plurality of spokes.

4. The apparatus of claim 1, wherein the cylinder ring moving away from the handle on the suture column corresponds with a collapsing of the plurality of spokes.

5. The apparatus of claim 1, wherein the plurality of spokes comprises radial spokes and vertical spokes.

6. The apparatus of claim 1, further comprising a plurality of blades operated by a trigger.

7. The apparatus of claim 1, the tie-bands are capable of compressing around the sutures.

8. The apparatus of claim 1, wherein the cylinder ring is comprised of one or more pieces.

9. The apparatus of claim 1, wherein the apparatus deploys the plurality of needles when one of the one or more triggers is depressed.

10. The apparatus of claim 1, wherein the handle is releasably attached to the suture column.

11. A kit for suturing a valve to a tissue comprising a replacement valve and the apparatus of claim 1.

12. A system for suturing a valve to a tissue comprising a replacement valve and the apparatus of claim 1.

13. A method for suturing a tissue comprising accessing a tissue of a patient; and suturing the tissue of the patient using the apparatus of claim 1.

14. A method for suturing a valve to a tissue comprising
making an incision in a patient;
inserting a replacement valve;
attaching the replacement valve to a tissue of the patient using the apparatus of claim 1; and
closing the incision in the patient.

15. The method of claim 14, wherein attaching the replacement valve to a tissue comprises deployment of the plurality of needles.

* * * * *